(12) United States Patent
Tyber et al.

(10) Patent No.: US 10,383,737 B2
(45) Date of Patent: Aug. 20, 2019

(54) ANATOMICAL WEDGE IMPLANT

(71) Applicants: Jeffrey Tyber, Landing, NJ (US); Christopher Faresich, Denville, NJ (US)

(72) Inventors: Jeffrey Tyber, Landing, NJ (US); Christopher Faresich, Denville, NJ (US)

(73) Assignee: Tyber Medical, LLC, Bethlehem, PA (US)

( * ) Notice: Subject to any disclaimer, the term of this patent is extended or adjusted under 35 U.S.C. 154(b) by 0 days.

(21) Appl. No.: 15/646,497

(22) Filed: Jul. 11, 2017

(65) Prior Publication Data

US 2018/0008419 A1 Jan. 11, 2018

Related U.S. Application Data

(63) Continuation-in-part of application No. 15/213,935, filed on Jul. 19, 2016, now Pat. No. 10,058,431.
(Continued)

(51) Int. Cl.
*A61F 2/44* (2006.01)
*A61F 2/30* (2006.01)
(Continued)

(52) U.S. Cl.
CPC ...... *A61F 2/30771* (2013.01); *A61B 17/8095* (2013.01); *A61B 17/8852* (2013.01); *A61B 90/94* (2016.02); *A61F 2/28* (2013.01); *A61F 2/4225* (2013.01); *A61F 2/44* (2013.01); *A61F 2/447* (2013.01); *A61F 2/4455* (2013.01); *A61F 2/4465* (2013.01); *A61F 2/4603* (2013.01); *A61F 2/4606* (2013.01); *A61F 2/4611* (2013.01); *A61L 31/088* (2013.01); *A61L 31/14* (2013.01); *A61L 31/18* (2013.01); *A61B 17/7059* (2013.01); *A61B 2017/565* (2013.01); *A61F 2002/2817* (2013.01); *A61F 2002/2835* (2013.01); *A61F 2002/3008* (2013.01); *A61F 2002/3009* (2013.01); *A61F 2002/30013* (2013.01); *A61F 2002/30029* (2013.01); *A61F 2002/3082* (2013.01); *A61F 2002/3092* (2013.01); *A61F 2002/3093* (2013.01); *A61F 2002/30266* (2013.01);
(Continued)

(58) Field of Classification Search
CPC ...... A61F 2/4455; A61F 2/446; A61F 2/4465; A61F 2/447; A61F 2/4611; A61F 2/4606; A61F 2/44; A61F 2/4225; A61B 17/808; A61B 17/8095; A61B 17/7059
See application file for complete search history.

(56) References Cited

U.S. PATENT DOCUMENTS

| | | | |
|---|---|---|---|
| 2005/0240267 A1* | 10/2005 | Randall | A61F 2/44 623/17.11 |
| 2008/0300634 A1* | 12/2008 | Gray | A61B 17/7059 606/280 |
| 2009/0048675 A1* | 2/2009 | Bhatnagar | A61B 17/0642 623/17.16 |

* cited by examiner

*Primary Examiner* — Si Ming Ku
(74) *Attorney, Agent, or Firm* — Joseph E. Maenner; Maenner & Associates, LLC

(57) ABSTRACT

An osteotomy implant includes a first surface extending generally in a first plane and a second surface extending generally in a second plane, oblique to the first plane. The first surface has a perimeter having a first linear edge, a first curve edge connected to the first linear edge, a second linear edge connected to the first curved edge, and a second curved edge connected to the second liner edge.

12 Claims, 23 Drawing Sheets

Related U.S. Application Data which is a continuation-in-part of application No. 15/162,657, filed on May 24, 2016, which is a continuation-in-part of application No. 14/948,322, filed on Nov. 22, 2015, now Pat. No. 10,201,433, which is a continuation-in-part of application No. 14/513,300, filed on Oct. 14, 2014, which is a continuation-in-part of application No. 14/054,100, filed on Oct. 15, 2013, now Pat. No. 9,387,087.

(60) Provisional application No. 61/715,891, filed on Oct. 19, 2012.

(51) Int. Cl.

| | | |
|---|---|---|
| *A61B 17/80* | (2006.01) | |
| *A61F 2/28* | (2006.01) | |
| *A61F 2/42* | (2006.01) | |
| *A61F 2/46* | (2006.01) | |
| *A61B 17/88* | (2006.01) | |
| *A61B 90/94* | (2016.01) | |
| *A61L 31/08* | (2006.01) | |
| *A61L 31/14* | (2006.01) | |
| *A61L 31/18* | (2006.01) | |
| *A61B 17/56* | (2006.01) | |
| *A61B 17/70* | (2006.01) | |

(52) U.S. Cl.
CPC .............. *A61F 2002/30281* (2013.01); *A61F 2002/30321* (2013.01); *A61F 2002/30326* (2013.01); *A61F 2002/30355* (2013.01); *A61F 2002/30433* (2013.01); *A61F 2002/30509* (2013.01); *A61F 2002/30523* (2013.01); *A61F 2002/30556* (2013.01); *A61F 2002/30578* (2013.01); *A61F 2002/30579* (2013.01); *A61F 2002/30622* (2013.01); *A61F 2002/30714* (2013.01); *A61F 2002/30774* (2013.01); *A61F 2002/30794* (2013.01); *A61F 2002/30808* (2013.01); *A61F 2002/30831* (2013.01); *A61F 2002/30836* (2013.01); *A61F 2002/30843* (2013.01); *A61F 2002/30904* (2013.01); *A61F 2002/4228* (2013.01); *A61F 2002/4475* (2013.01); *A61F 2002/4623* (2013.01); *A61F 2002/4627* (2013.01); *A61F 2310/00407* (2013.01); *A61F 2310/00461* (2013.01); *A61F 2310/00796* (2013.01); *A61L 2430/02* (2013.01)

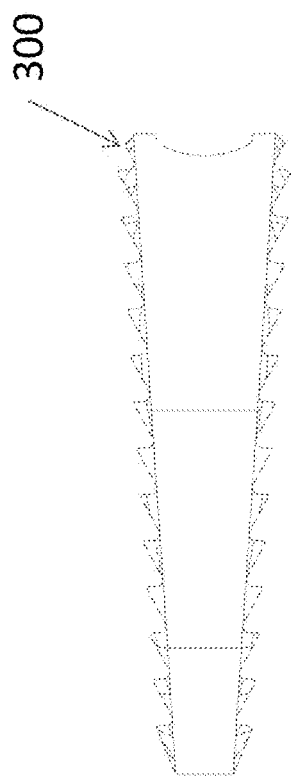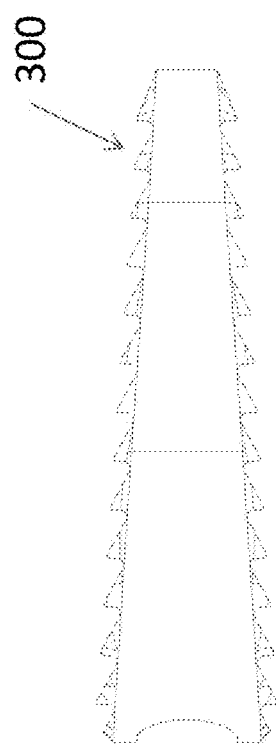
FIG. 18
FIG. 19

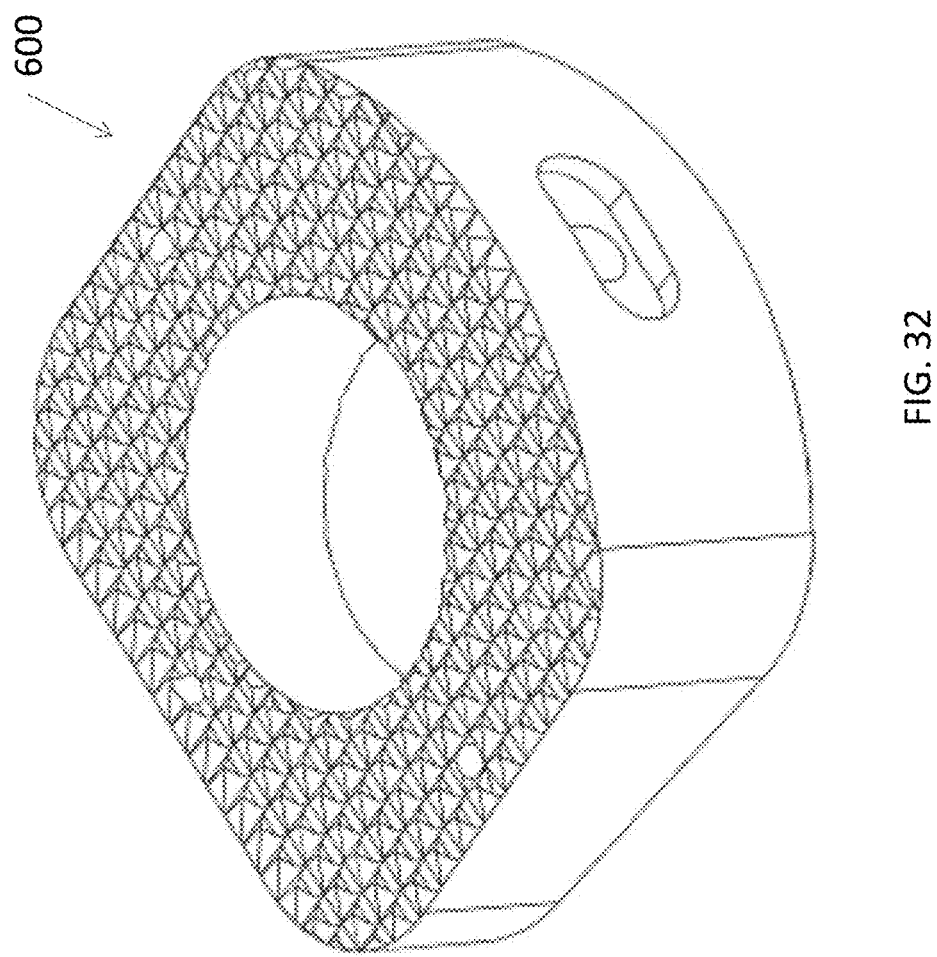

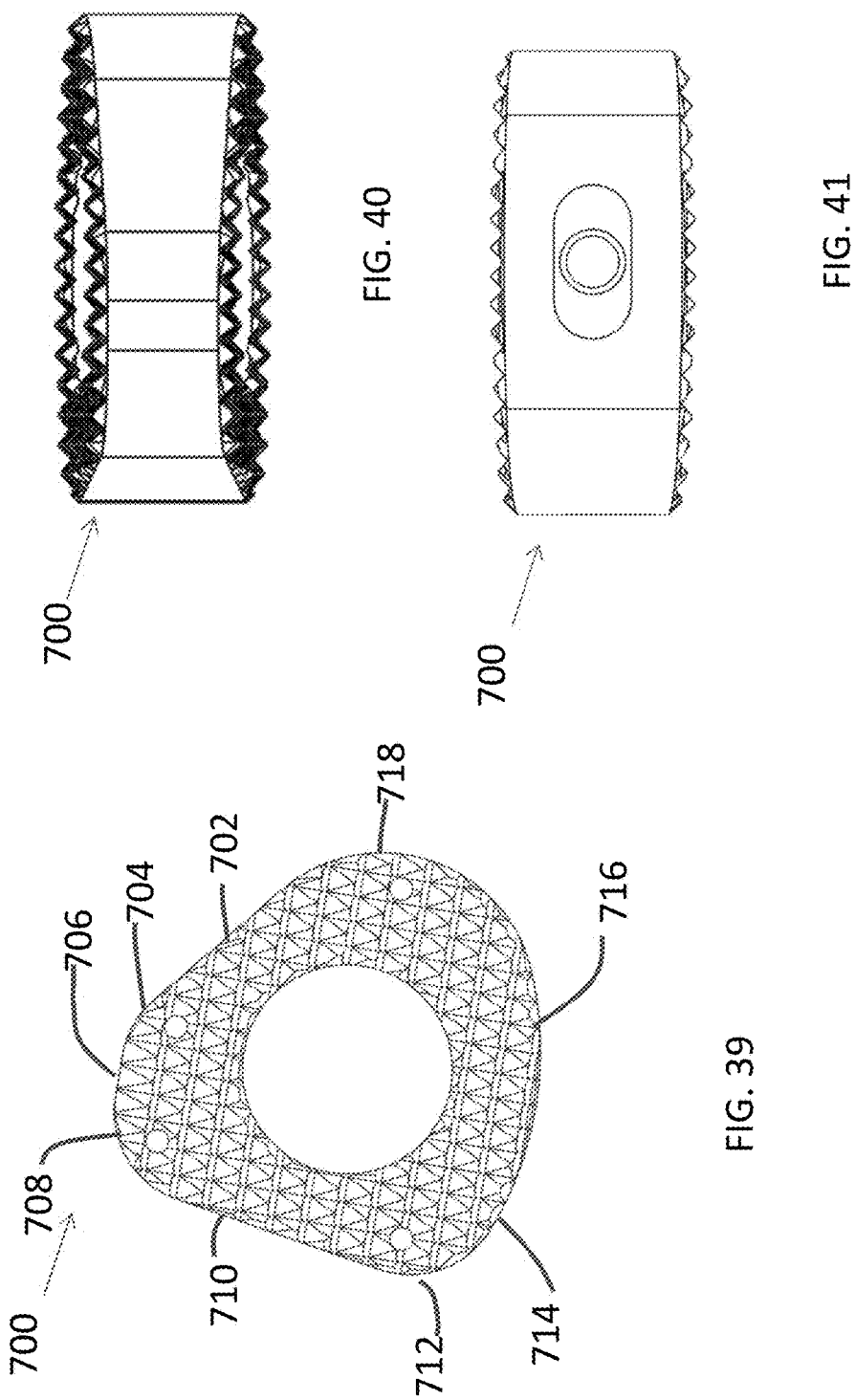

ANATOMICAL WEDGE IMPLANT

CROSS-REFERENCE TO RELATED APPLICATIONS

The present application is a continuation-in-part of co-pending application Ser. No. 15/213,935, filed on Jul. 19, 2016, which is a continuation-in-art of co-pending application Ser. No. 15/162,657, filed on May 24, 2016, which is a continuation-in-part of application Ser. No. 14/948,322, filed on Nov. 22, 2015, which is a continuation-in-part of co-pending application Ser. No. 14/513,300, filed on Oct. 14, 2014, which is a continuation-in-part application of U.S. patent application Ser. No. 14/054,100, filed on Oct. 15, 2013 and issued on Jul. 12, 2016 as U.S. Pat. No. 9,387,087, which claims priority from U.S. Provisional Patent Application Ser. No. 61/715,891, filed on Oct. 19, 2012, all of which are incorporated by reference herein in their entireties.

BACKGROUND OF THE INVENTION

Field of the Invention

The present invention generally relates to a wedge implant that is inserted into an osteotomy incision to stabilize and reposition a portion of bone.

Description of the Related Art

An osteotomy is a surgical procedure that typically involves cutting and some times removing a portion of bone, such as, for example, the calcaneus. Wedge osteotomies utilize a wedge implant to reposition and stabilize the bone on either side of the cut.

Typically, osteotomy wedge implants are constructed from inert biocompatible material such as titanium or polyether-ether-ketone (PEEK). Titanium is typically used in orthopedic systems due to its strength and osteoconductive properties. However, in intervertebral spacers, titanium is not the preferred choice due to its high stiffness compared with bone. The large stiffness differential between bone and titanium has caused a high incidence of subsidence of the implant into the vertebral body. This has led the way for other biomaterials being selected for the spacer's body material. PEEK is a common interbody material selected because the Young's Modulus is extremely similar to bone and the material is extremely inert. However, PEEK is not an osteoconductive material and a large central oval cavity is the only space designed for bone through growth, thus the spacers remove a larger percentage of the fusion area.

Prior art wedge implants, such as, for example, the Arthrex product line, feature a metatarsal opening wedge plate system in which the plate is secured over the osteotomy and a bone wedge is implanted into the osteotomy space. One perceived problem with this open wedge osteotomy system is the loss of bone correction due to mechanical failure of the bone implant.

The Wright Medical BIOFOAM Wedge System provides a porous titanium wedge implant. The procedure using this system involves opening in osteotomy, implanting the wedge into the bone space, and then securing a plate over the osteotomy site. One perceived problem with this system is the radiolucency of the porous titanium implants. The titanium implant shows up during MRI, CT, and x-ray scans, making postoperative imaging impossible.

The Arthrex OSferion System provides a synthetic, porous β-TCP bone wedge for femoral and tibial wedge osteotomies. The OSferion bone wedge is constructed from an osteoconductive bone graft substitute and a β-TCP bone void filler.

It would be beneficial to provide an osteotomy wedge implant that is radio transparent, to enable a clinician to view phone on either side of the wedge implant, and osteoconductive, to maximize the bone fusion area.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is an osteotomy implant having a first surface extending generally in a first plane and a second surface extending generally in a second plane, oblique to the first plane. The first surface has a perimeter having a first linear edge, a first curve edge connected to the first linear edge, a second linear edge connected to the first curved edge, and a second curved edge connected to the second liner edge.

In another embodiment, an osteotomy implant system includes a generally wedge shaped core constructed from a radio translucent material. The body has a central plane extending therethrough. A first generally planar bone engaging surface extends at an acute angle relative to the central plane on a first side of the core and a second generally planar bone engaging surface is disposed on an opposing side of the central plane from the first generally planar bone engaging surface on a second side of the core. The second generally planar bone engaging surface extends at the acute angle relative to the central plane. The first surface has a perimeter has a linear edge, and a curved edge connecting each end of the linear edge, the curved edge having at least four different radii of curvature.

In still another embodiment, a method of inserting a wedge to stabilize and reposition a bone comprises the steps of making at least a partial cut in a bone at an osteotomy site; and inserting a wedge into the cut, the wedge having an osteoconductive coating.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 18 is a right side elevational view of the wedge osteotomy implant of FIG. 14;

FIG. 19 is a left side elevational view of the wedge osteotomy implant of FIG. 14;

FIG. 32 is a perspective view of a sixth exemplary embodiment of an osteotomy wedge implant according to the present invention;

FIG. 39 is a top plan view of the wedge osteotomy implant of FIG. 38, with the bottom plan view being identical;

FIG. 40 is a front elevational view of the wedge osteotomy implant of FIG. 38;

FIG. 41 is a rear elevational view of the wedge osteotomy implant of FIG. 38;

DETAILED DESCRIPTION

Figure 1:
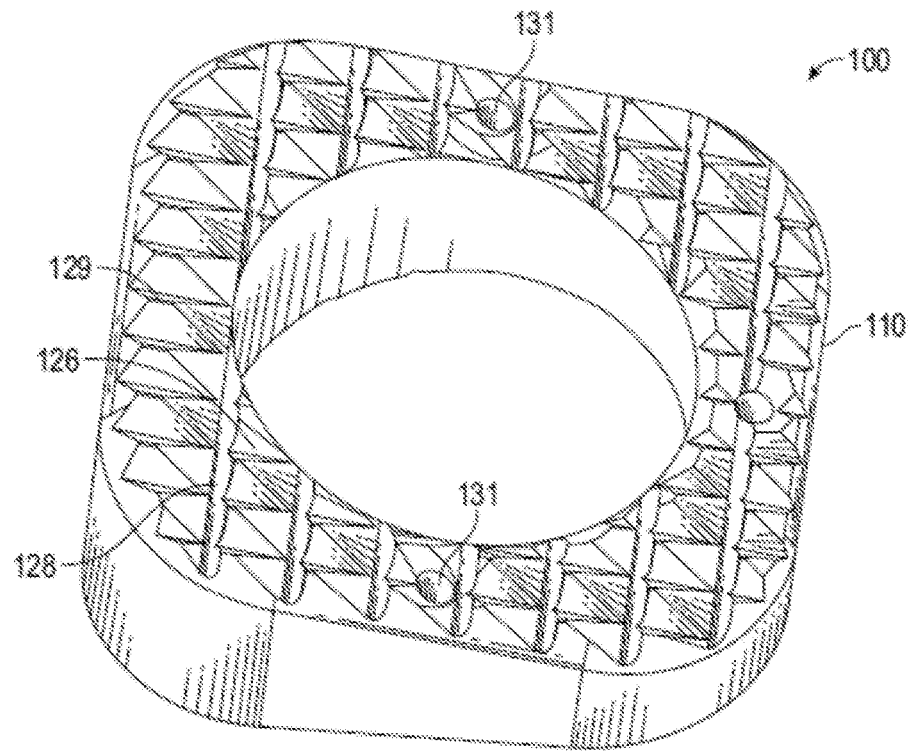
FIG. 1 is a perspective view of an osteotomy implant according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The terminology includes the words specifically mentioned, derivatives thereof and words of similar import.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to FIGS. 1-7, an osteotomy wedge system according to the present invention is disclosed. The wedge system can be used for internal fixation of bone fractures, fusions, or osteotomies in lower limbs, such as, for example, tibial osteotomies, Evans osteotomies, metatarsal/cuneiform arthrodesis, Cotton osteotomies, as well as other indications.

The inventive wedge system provides a fusion site for bone to grow into an osteotomy wedge to secure the wedge into an incision that is formed in the bone into which the wedge is inserted. The wedge helps to stabilize the bone and to properly orient the bone. The fusion site secures the wedge to the bone as the bone continues to grow.

Figure 2:
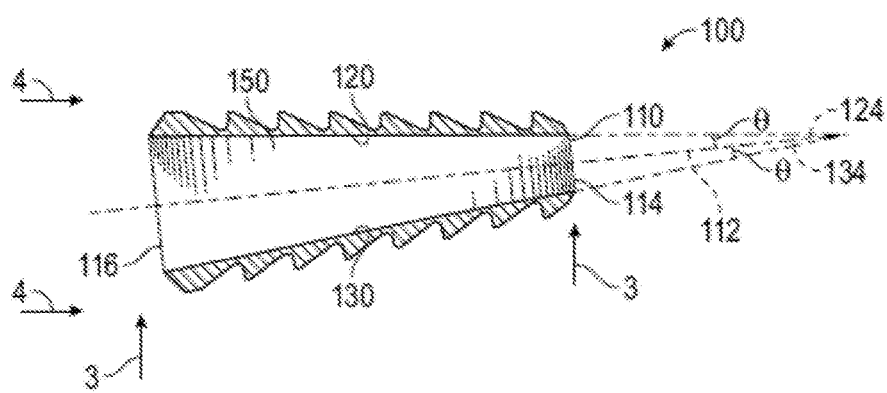
FIG. 2 is a side elevational view of the osteotomy implant shown in FIG. 1.

Referring to FIGS. 1-4, the wedge system includes a wedge 100 having a body 110 that is generally bisected by a central plane 112. A top plan view of body 110, shown in FIG. 2, shows that body 110 has rounded corners and cavity 113 extending all of the way therethrough. Cavity 113 provides for the optional insertion of graft material (not shown).

Body 110 is generally wedge-shaped with a thinner medial portion 114 sized to be inserted toward an interior portion of a cut bone 50, and a wider peripheral portion 116, forming a trailing face that is sized to extend toward an exterior of the cut bone 50. Body 110 includes a first surface 120, an opposing second surface 130, and a core 150 disposed between first surface 120 and a second surface 130.

Figure 2A:
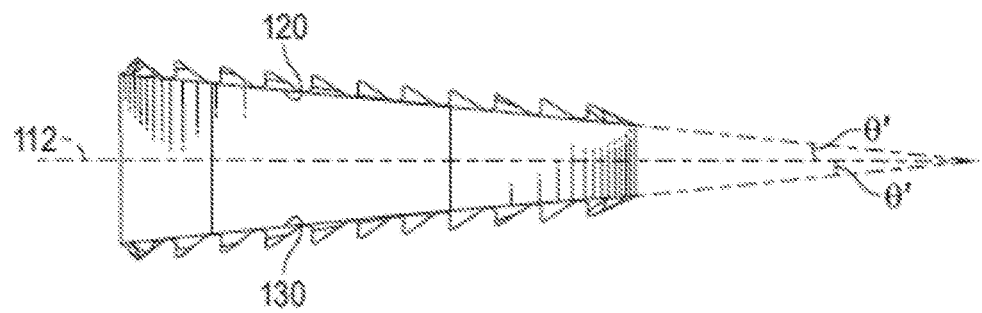
FIG. 2A is a side elevational view of an osteotomy implant with a larger angle than the implant shown in FIG. 2.
Figure 2B:
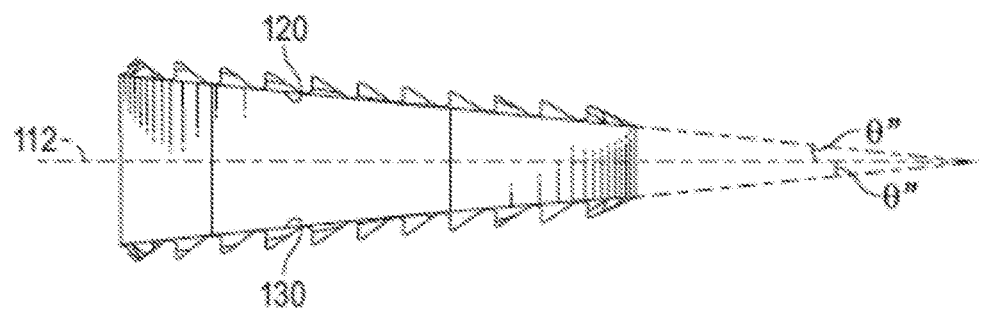
FIG. 2B is a side elevational view of an osteotomy implant with a larger angle than the implant shown in FIG. 2A.
Figure 3:
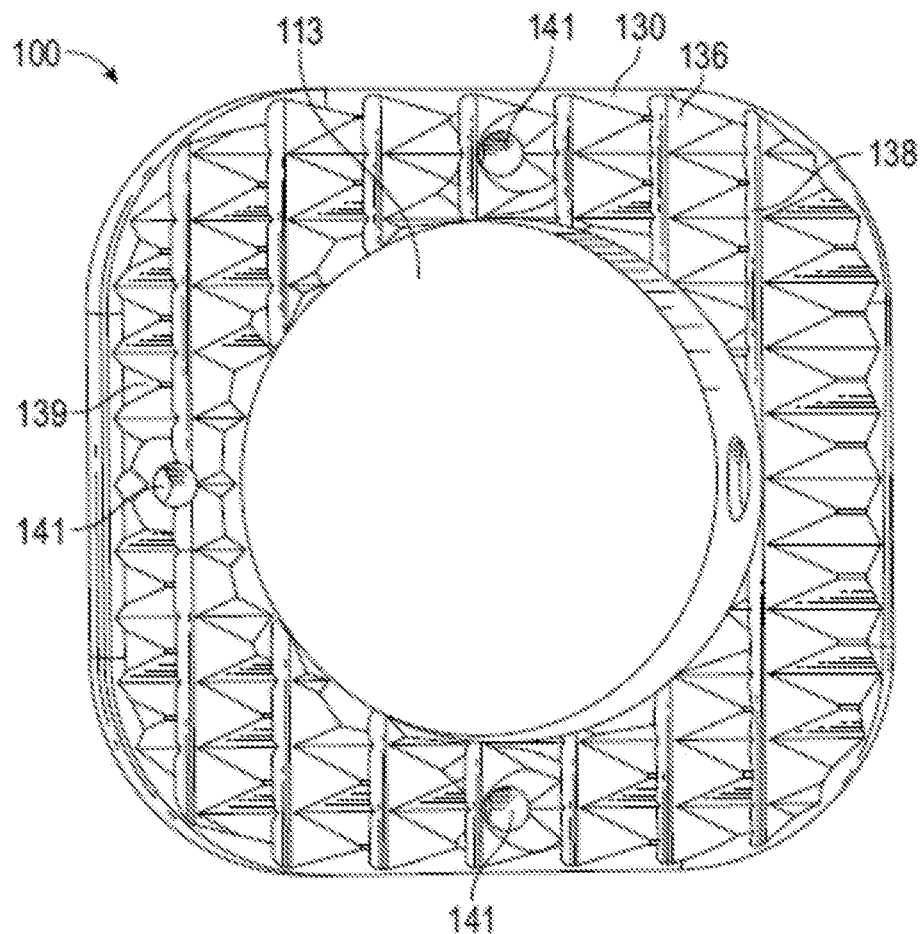
FIG. 3 is a bottom plan view of the osteotomy implant shown in FIG. 2, taken along lines 3-3 FIG. 2.

A first surface 120 extends between medial portion 114 and lateral portion 116 generally in a first plane 124 that extends obliquely at an acute angle θ relative to central plane 112. As shown in FIGS. 2, 2A, and 2B, different angles θ, θ', θ" can be provided, depending on the amount of angular correction required in a particular bone.

First surface 120 has a first plurality of longitudinal grooves 126 and a second plurality of transverse grooves 128 extending therealong. Portions of first surface 120 extend between adjacent longitudinal grooves 126 and transverse grooves 128 form individual peaks or pyramidal shaped teeth 129.

Similarly, a second surface 130 extends on an opposite side of central plane 112 from first surface 120, also at an acute angle θ relative to central plane 112. As shown in FIGS. 2A-2C, different angles θ, θ', θ" can be provided, depending on the amount of angular correction required in a particular bone.

Second surface 130 has a first plurality of longitudinal grooves 136 and a second plurality of transverse grooves 138 extending therealong. Portions of second surface 130 extend between adjacent longitudinal grooves 136 and transverse grooves 138 form individual peaks or pyramidal shaped teeth 139.

Each of first surface 120 and second surface 130 includes a osteoconductive coating, such as, for example, a titanium plasma spray coating, that has a thickness of between about 2 microns and about 500 microns. The spray coating is sufficiently thin, such that first surface 120 and second surface 130 do not interfere with imaging methods, and are therefore largely transparent to imagery.

Alternatively, the spray coating can be sufficiently thick to enable peripheral visibility of first surface 120 and second surface 130 without affecting the visibility of core 150 via imaging, in order to allow the progress of bone growth to be viewed. As an alternative to titanium, tantalum, nitinol, or other biocompatible osteoconductive coating can be used. Further, to enable visualization of the implant, radiopaque markers 131 are provided on first surface 120 of wedge 100. In an exemplary embodiment, three markers 131 are provided around the periphery of wedge 100 to define the location and orientation of wedge 100 after implantation. Similarly, radiopaque markers 141 are provided on second surface 130 of wedge 100.

First surface 120 and second surface 130 can each be a highly roughened exterior surface to provide an environment conducive to early stability and to ensure intimate osseointegration between bone 50 (shown in FIGS. 6 and 7) and wedge 100. The roughened surface has an average surface roughness (Ra) greater than 0.006 about microns.

In an exemplary embodiment, core 150 can be constructed from a radiolucent or a partially radiolucent material, such as, for example, PEEK or a porous PEEK, such as is manufactured by Vertera Spine of Atlanta, Ga., and is transparent or at least translucent on MRI, CT, and x-ray imaging.

Core 150 has the same Young's modulus as bone, namely, about 3.6 GigaPascals (GPa), which prevent shielding in bone 50, while also maintaining superior mechanical properties. In an exemplary embodiment, core 150 having a Young's modulus between about 0.5 GPa and about 18 GPa can be used. FIG. 2 shows a PEEK core 150 with osteoconductive (titanium plasma spray) surfaces 120, 130 and their respective peaks 129, 139. Alternatively, core 150 can be constructed using a composite of osetoconductive and non-osteoconductive material, or other biocompatible material. Additionally, wedge 100 can have a core 150 constructed from any of the above referenced materials, with bone engaging surfaces being formed with an osteoconductive structure attached to or around core 150.

In an exemplary embodiment, core 150 can be 3D printed from a plurality of materials such that core 150 is at least partially radiolucent, yet is also constructed with an osteoconductive surface, without the need to separately spray an osteoconductive layer onto core 150. Optionally, a hydroxyapatite coating can be applied on surfaces 114, 116 and on the walls of cavity 113 to enhance for visualization of wedge 100 after implementation.

Figure 4:
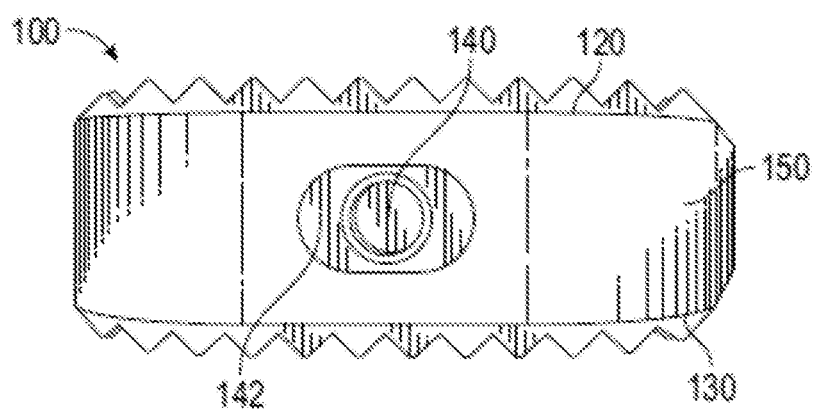
FIG. 4 is a lateral side elevational view of the osteotomy implant shown in FIG. 2, taken along lines 4-4 of FIG. 2.

As shown in FIG. 4, lateral portion 116 includes an aperture 140 that is centrally located within a recess 142 between first surface 120 and second surface 130. Aperture 140 can be configured in either a threaded configuration, interference configuration or any means to secure the body 110 to a separate insertion instrument 1000 (discussed in more detail below). In the embodiment of wedge 100 shown in FIG. 4, aperture 140 has blind threads.

In the exemplary embodiment shown FIG. 4, recess 142 is generally oblong in shape to prevent rotation of wedge 100 with respect to insertion instrument 1000 implantation of wedge 100 into bone 50.

Figure 5:
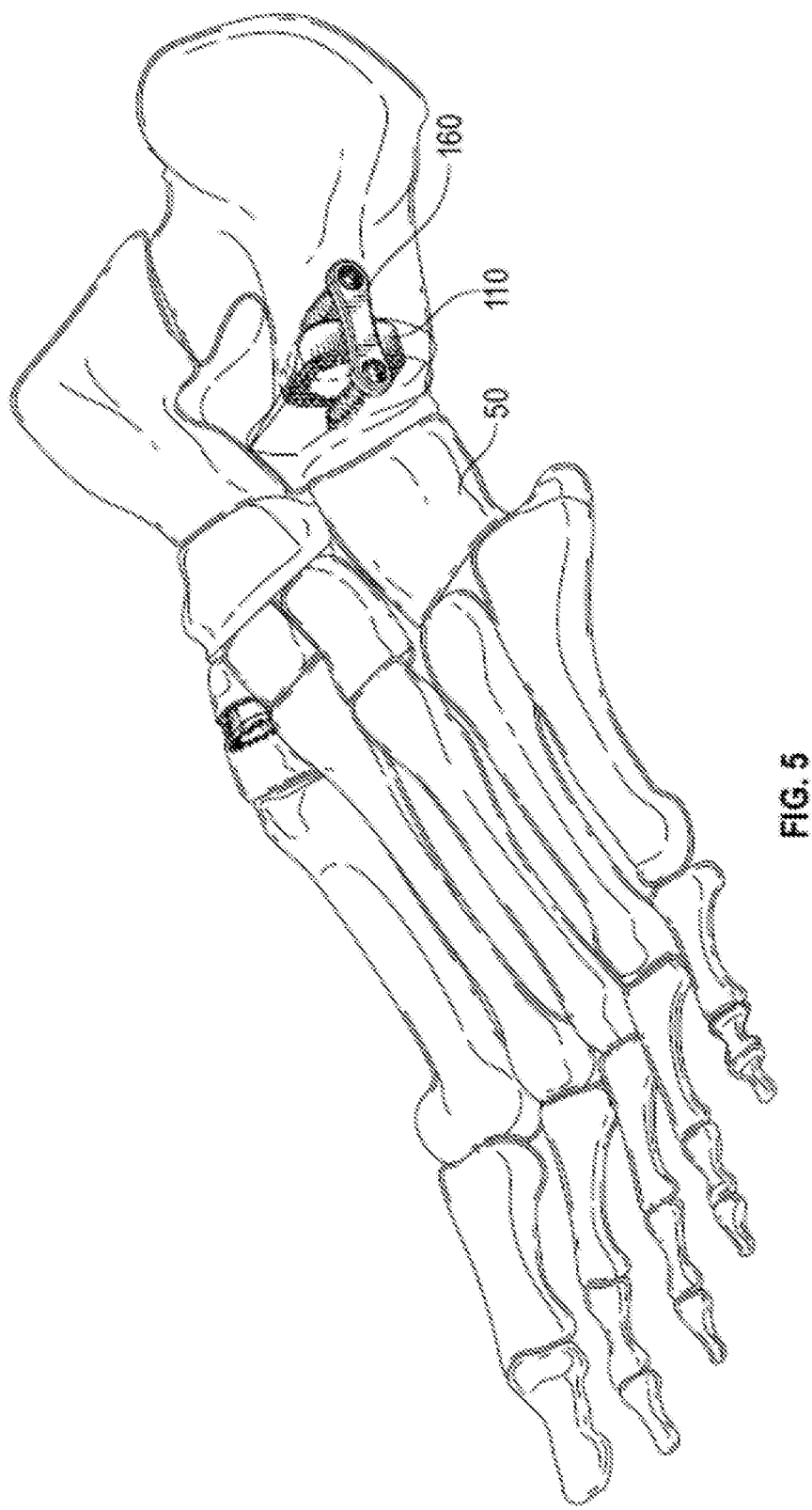
FIG. 5 is a perspective view of the osteotomy implant shown in FIGS. 1-4 inserted into a bone of a foot.
Figure 6:
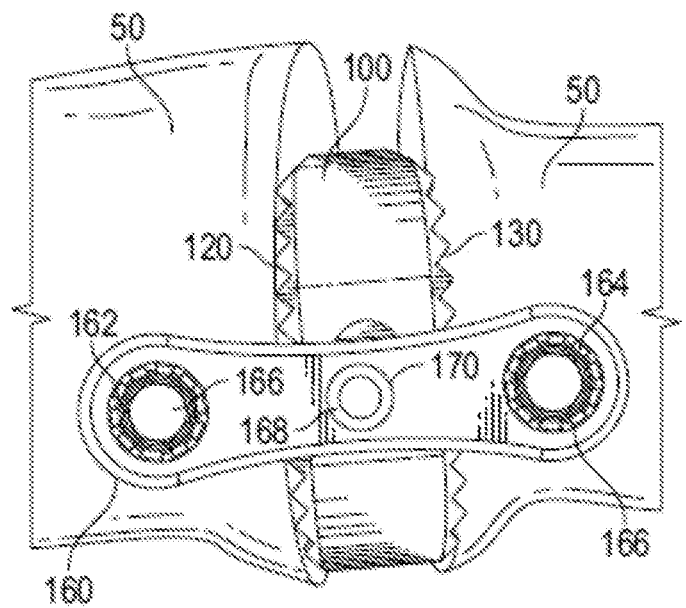
FIG. 6 is an enlarged lateral side elevational view of the osteotomy implant shown in FIG. 5.
Figure 7:
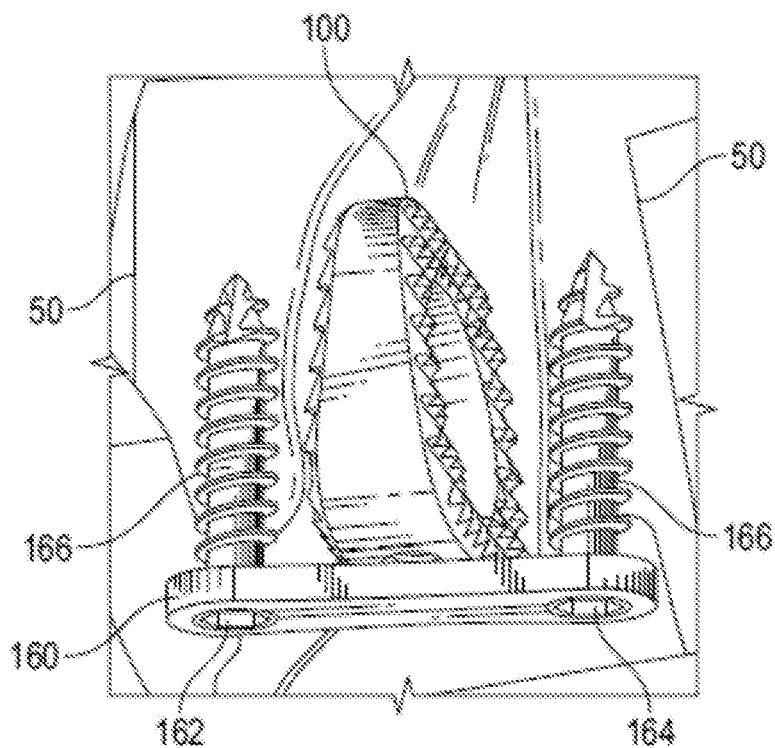
FIG. 7 is an enlarged top plan view of the osteotomy implant and faceplate shown in FIG. 5.
Figure 8:
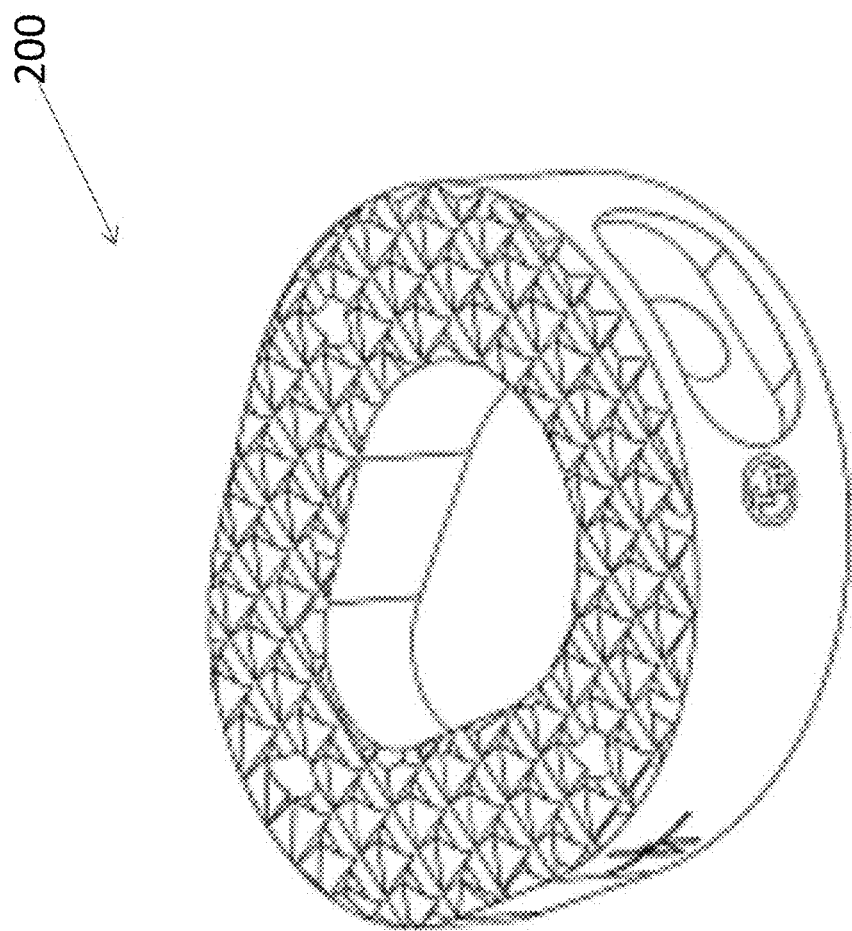
FIG. 8 is a perspective view of a second exemplary embodiment of an osteotomy wedge implant according to the present invention.
Figure 10:
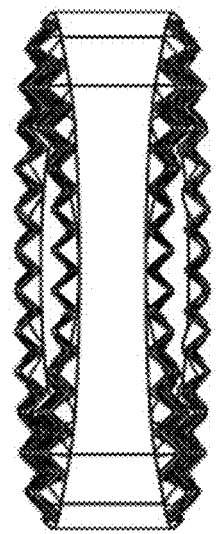
FIG. 10 is a front elevational view of the wedge osteotomy implant of FIG. 8.
Figure 11:
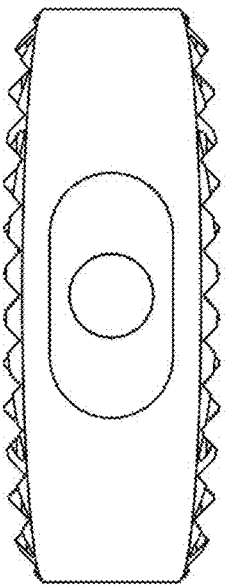
FIG. 11 is a rear elevational view of the wedge osteotomy implant of FIG. 8.

As shown in FIGS. 5-7, the inventive osteotomy wedge system optionally includes a fixation plate 160 that is attached to bone 50 over wedge 100 after wedge 100 is inserted into bone 50. Plate 160 has a first hole 162 and a second hole 164 formed therein. A length between first hole 162 and second hole 164 is greater than a length between first surface 120 and the second surface 130 such that wedge 100 is located between first hole 162 and second hole 164 so that bone fixation screws 166 can be inserted through first hole 162 and second hole 164, and into bone 50 to secure plate 162 bone 50 on either side of wedge 100.

An exemplary method of inserting wedge 100 to stabilize and reposition a bone will now be discussed. First, a cut is made in bone 50 at an osteotomy site. Typically, the cut is only a partial cut, such that a portion of bone 50 on either side of the cut remains connected. Next, a forked wedge tool (not shown) is inserted into the cut and is used to open the osteotomy site. With insertion instrument 1000 that is disclosed in U.S. patent application Ser. No. 14/054,100, filed on Oct. 15, 2013 and issued on Jul. 12, 2016 as U.S. Pat. No. 9,387,087, connected to wedge 100 at aperture 140, wedge 100 is inserted into the cut. When wedge 100 is properly positioned, insertion instrument 1000 is removed from wedge 100, leaving wedge 100 in the osteotomy site. Fixation plate 160 is applied over wedge 100 and secured to bone 50 on either side of wedge 100 by fixation screws 166. Alternatively, wedge 100 can be used to fix to adjacent bones to each other by prepping the bone surface of the adjacent bones at facing ends, and then inserting wedge 100 between the bones and securing wedge 100 to both bones with plate 160.

Optionally, if third hole 168 is present, fixation screw 170 can be inserted through third hole 168, and into aperture 140, securing fixation plate 160 directly to wedge 100.

Optionally, each device described above that is to be implanted (i.e., interbody, wedge, screws, plate, etc.) can be coated with an antimicrobial agent, such as, for example, silver oxide. The anti-microbial coating can be in the form of a nano coating or other type of coating. Such an antimicrobial coating can be used to reduce or eliminate infections within the patient.

Wedges according to the present invention can have various sizes and shapes of outer perimeters to conform to the size and shape of the bone into which the wedge is being implanted in order to provide sufficient contact between both sides of the bone and the wedge, without any portion of the wedge protruding exteriorly from the bone. Alternatively, wedges according to the present invention can have sizes and shapes such that at least 50% of the perimeter of the wedge is contained within an osteotomy site.

Different exemplary embodiments of wedges according to the invention are described below. As described below, edges are located between and connected to the edges described immediately before and after the edge description. Also, the last edge portion of each embodiment is connected to the first edge portion of that embodiment.

Figure 9:
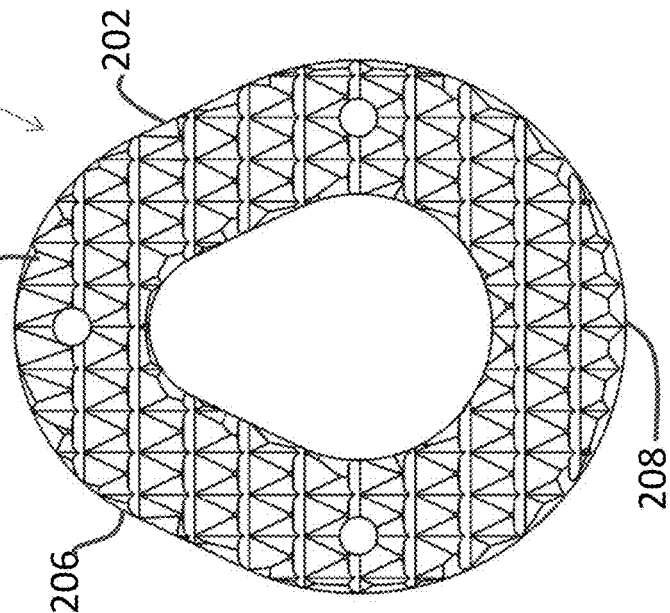
FIG. 9 is a top plan view of the wedge osteotomy implant of FIG. 8, with the bottom plan view being identical.
Figure 12:
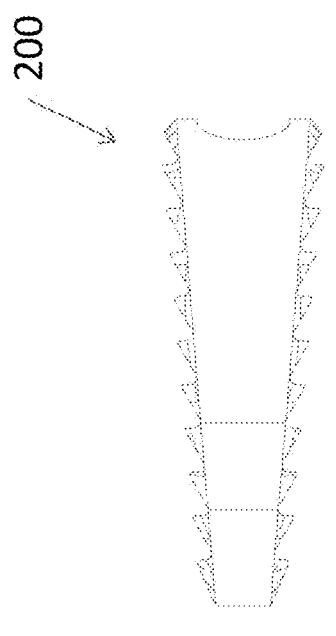
FIG. 12 is a right side elevational view of the wedge osteotomy implant of FIG. 8.
Figure 13:
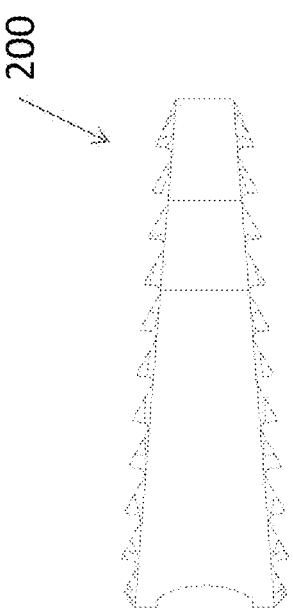
FIG. 13 is a left side elevational view of the wedge osteotomy implant of FIG. 8.
Figure 14:
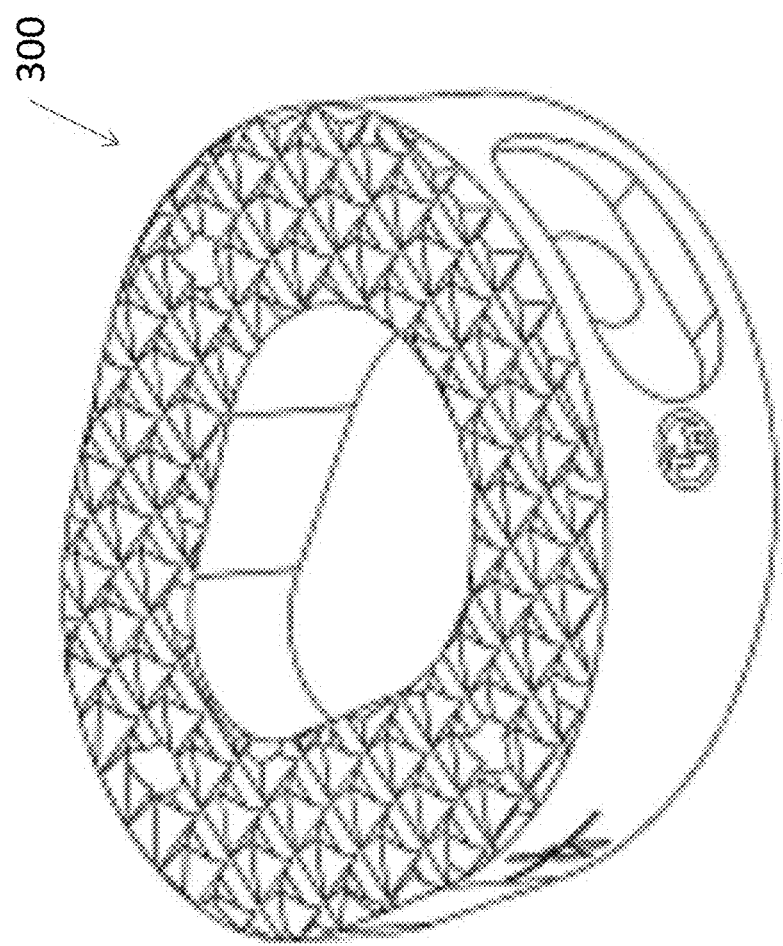
FIG. 14 is a perspective view of a third exemplary embodiment of an osteotomy wedge implant according to the present invention.
Figure 16:
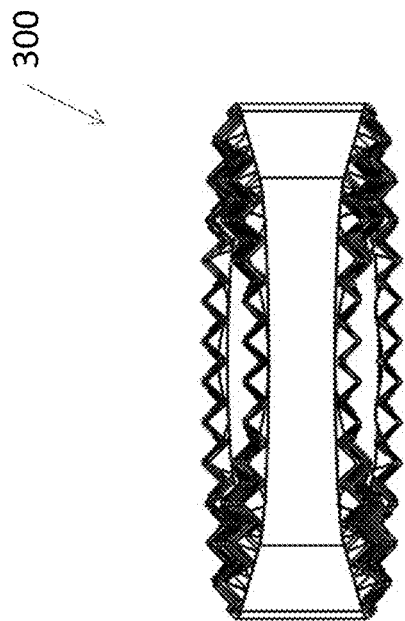
FIG. 16 is a front elevational view of the wedge osteotomy implant of FIG. 14.
Figure 17:
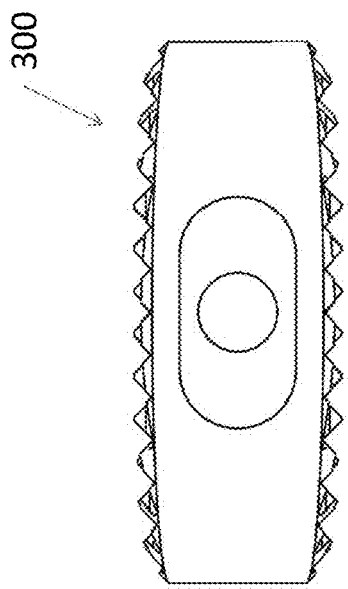
FIG. 17 is a rear elevational view of the wedge osteotomy implant of FIG. 14.

Referring now to FIGS. 8-13, an exemplary embodiment of a wedge 200 is shown. Referring specifically to FIG. 9, wedge 200 has a first linear edge 202, a first curved edge 204 having a first radius of curvature, a second linear edge 206, and a second curved edge 208 having second radius of curvature, different from the first radius of curvature. Wedge 200 is symmetrical about a longitudinal axis 210 through the first curved edge 204 and the second curved edge 208. In an exemplary embodiment, first linear edge 202 has a length of about 3.80 mm, first curved edge 204 has a radius of curvature of about 7 mm, second linear edge 206 has a length of about 3.80 mm, and second curved edge 208 has a radius of curvature of about 5.52 mm. Additionally, first curved edge 204 traces an arc of less than 180 degrees and second curved edge 208 traces an arc of greater than 180 degrees, resulting in linear edges 202, 206 being non-parallel to each other.

Figure 15:
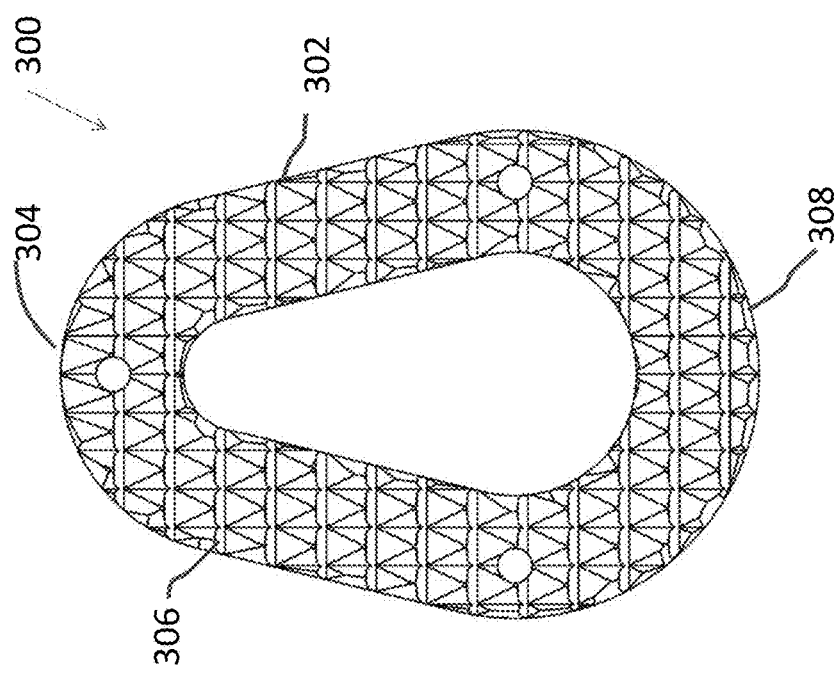
FIG. 15 is a top plan view of the wedge osteotomy implant of FIG. 14, with the bottom plan view being identical.
Figure 20:
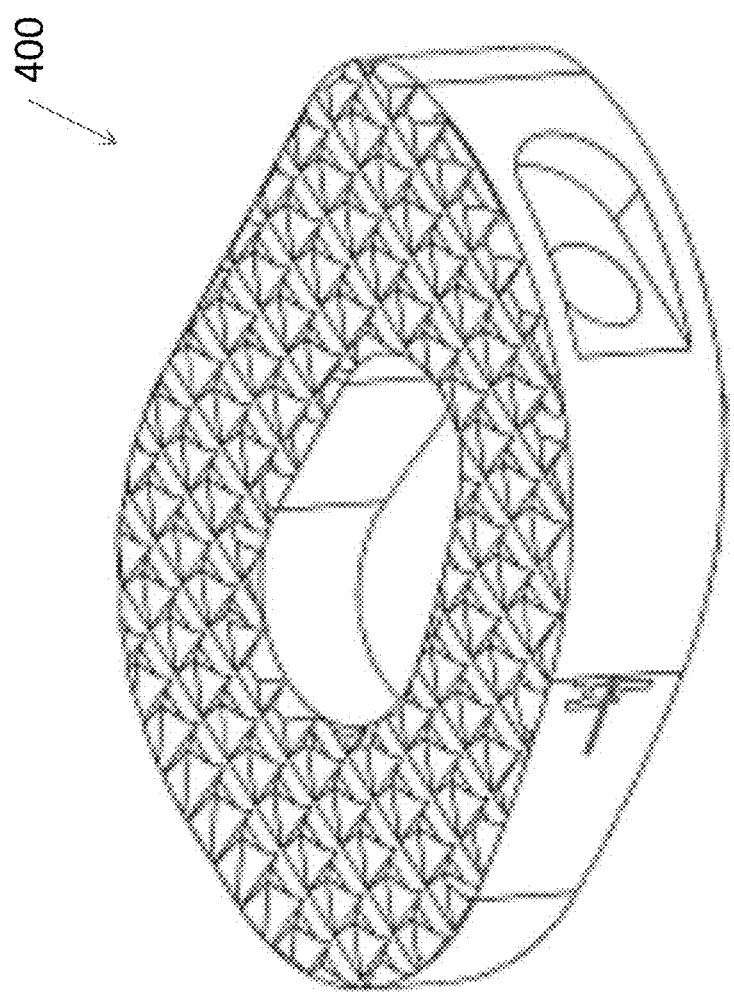
FIG. 20 is a perspective view of a fourth exemplary embodiment of an osteotomy wedge implant according to the present invention.
Figure 22:
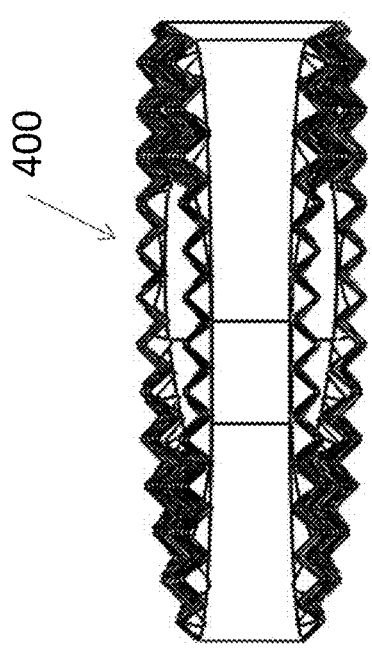
FIG. 22 is a front elevational view of the wedge osteotomy implant of FIG. 20.
Figure 23:
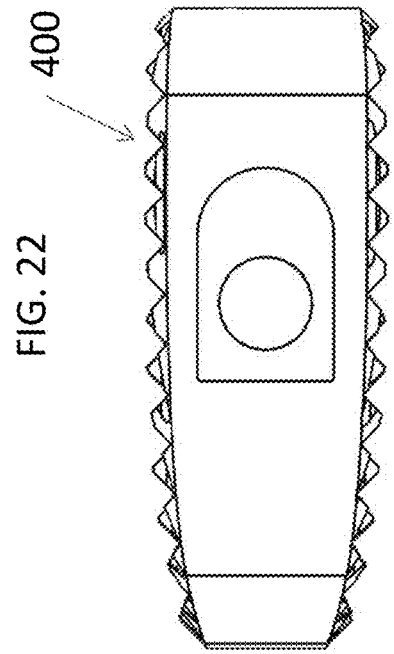
FIG. 23 is a rear elevational view of the wedge osteotomy implant of FIG. 20.

Referring now to FIGS. 14-19, an exemplary embodiment of a wedge 300 is shown. Referring specifically to FIG. 15, wedge 300 has a first linear edge 302, a first curved edge 304 having a first radius of curvature, a second linear edge 306, and a second curved edge 308 having second radius of curvature, different from the first radius of curvature. Wedge 300 is symmetrical about a longitudinal axis 310 through the first curved edge 304 and the second curved edge 308. In an exemplary embodiment, first linear edge 302 has a length of about 6.78 mm, first curved edge 304 has a radius of curvature of about 7 mm, second linear edge 306 has a length of about 6.78 mm, and second curved edge 308 has a radius of curvature of about 5.15 mm. Additionally, first curved edge 304 traces an arc of less than 180 degrees and second curved edge 308 traces an arc of greater than 180 degrees, resulting in linear edges 302, 306 being non-parallel to each other.

Figure 21:
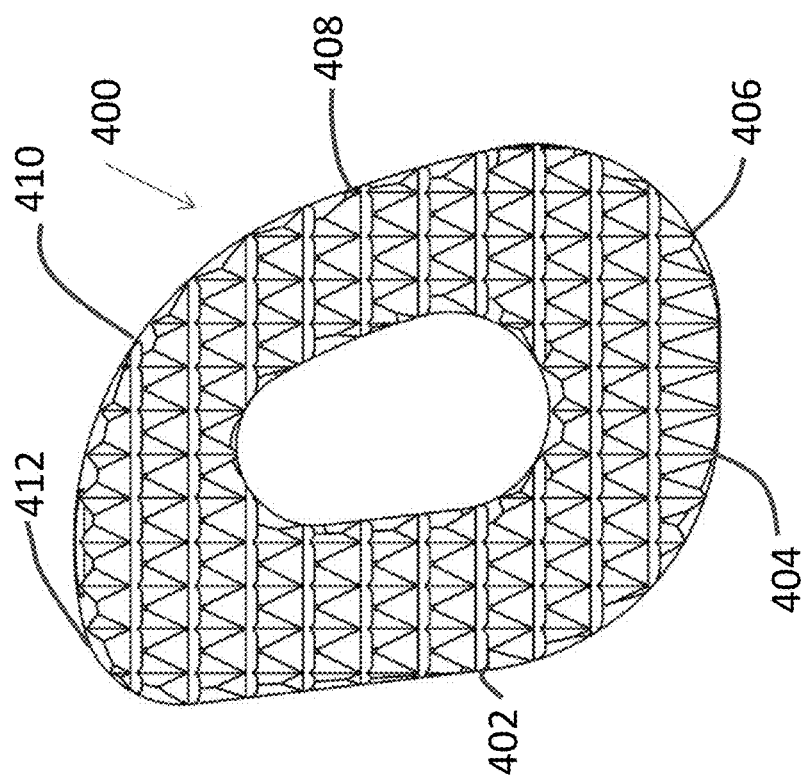
FIG. 21 is a top plan view of the wedge osteotomy implant of FIG. 20, with the bottom plan view being identical.
Figure 24:
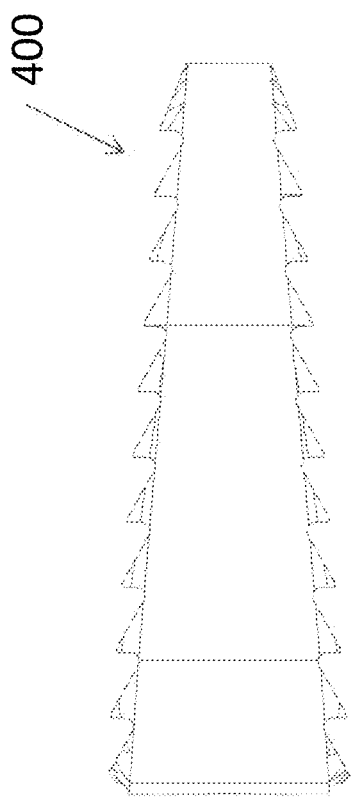
FIG. 24 is a right side elevational view of the wedge osteotomy implant of FIG. 20.
Figure 25:
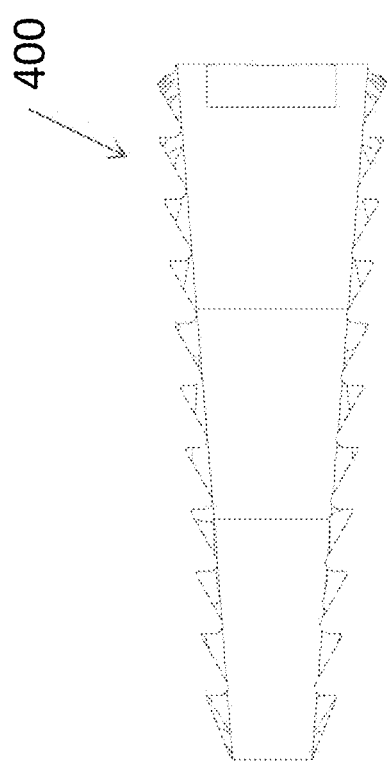
FIG. 25 is a left side elevational view of the wedge osteotomy implant of FIG. 20.
Figure 26:
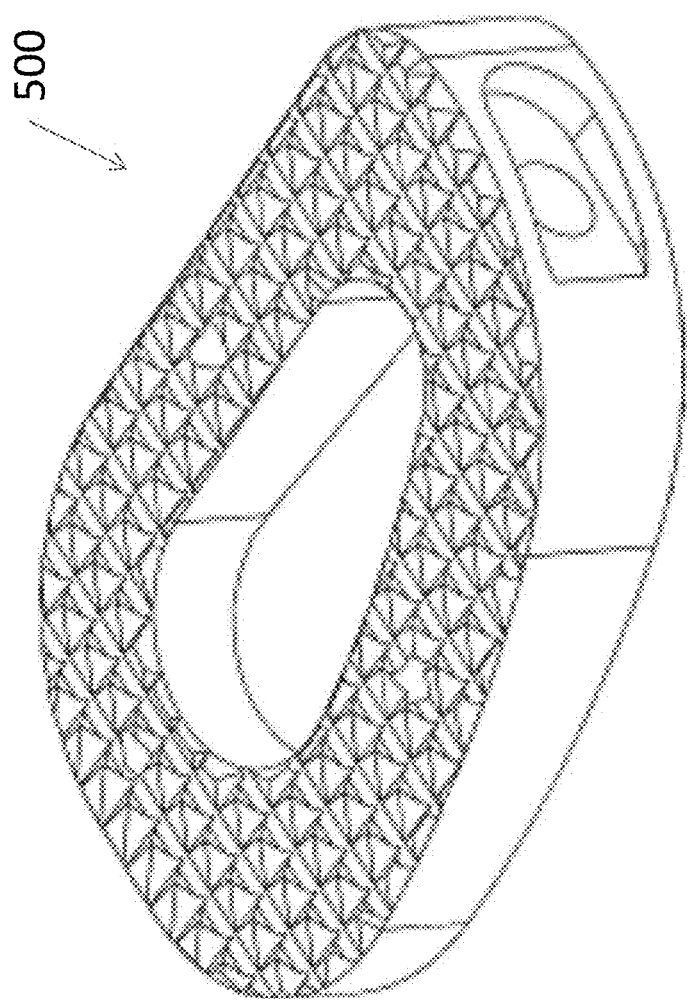
FIG. 26 is a perspective view of a fifth exemplary embodiment of an osteotomy wedge implant according to the present invention.
Figure 28:
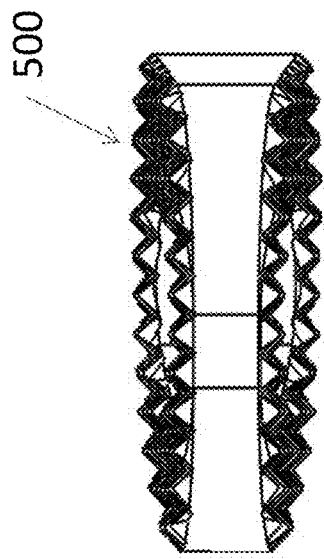
FIG. 28 is a front elevational view of the wedge osteotomy implant of FIG. 26.
Figure 29:
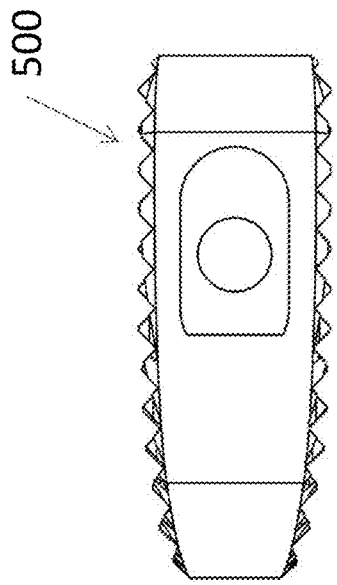
FIG. 29 is a rear elevational view of the wedge osteotomy implant of FIG. 26.

Referring now to FIGS. 20-25, an exemplary embodiment of a wedge 400 is shown. Referring specifically to FIG. 21, wedge 400 has a first linear edge 402, a first curved edge 404 having first radius of curvature, a second curved edge 406 having a second radius of curvature different from the first radius of curvature, a third curved edge 408 having a third radius of curvature different from the first and the second radii of curvature, a fourth curved edge 410 having a fourth radius of curvature, different from the first, second, and third radii of curvature, and a fifth curved edge 412, having a fifth radius of curvature, different from the first, second, third, and fourth radii of curvature. In an exemplary embodiment, first linear edge 402 has a length of about 7.27 mm, first curved edge 404 has a radius of curvature of about 6.56 mm, second curved edge 406 has a radius of curvature of about 4.63 mm, third curved edge 408 has a radius of curvature of about 30 mm, fourth curved edge 410 has a radius of curvature of about 9.09 mm, and fifth curved edge 412 has a radius of curvature of about 2.50 mm.

Figure 27:
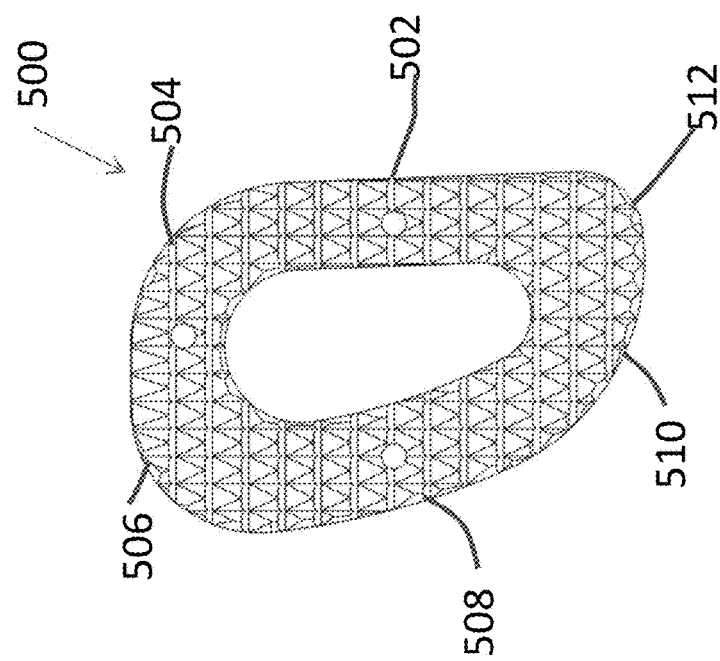
FIG. 27 is a top plan view of the wedge osteotomy implant of FIG. 26, with the bottom plan view being identical.
Figure 30:
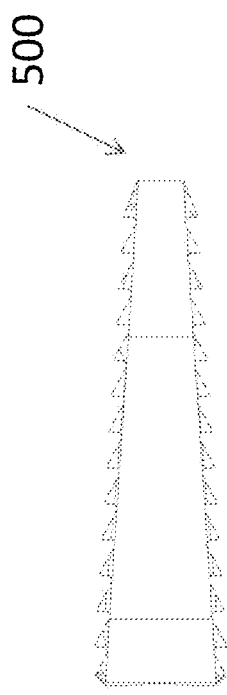
FIG. 30 is a right side elevational view of the wedge osteotomy implant of FIG. 26.
Figure 31:
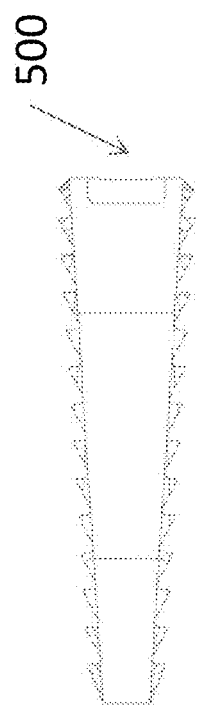
FIG. 31 is a left side elevational view of the wedge osteotomy implant of FIG. 26.
Figure 34:
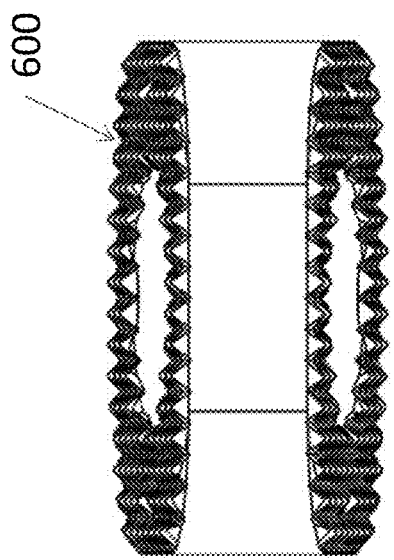
FIG. 34 is a front elevational view of the wedge osteotomy implant of FIG. 32.
Figure 35:
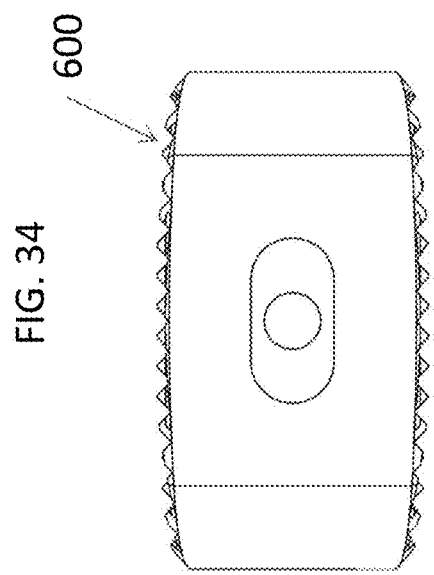
FIG. 35 is a rear elevational view of the wedge osteotomy implant of FIG. 32.

Referring now to FIGS. 26-31, an exemplary embodiment of a wedge 500 is shown. Referring specifically to FIG. 27, wedge 500 has a first linear edge 502, a first curved edge 504 having first radius of curvature, a second curved edge 506 having second radius of curvature different from the first radius of curvature, a third curved edge 508 having a third radius of curvature different from the first and the second radii of curvature, a fourth curved edge 510 having a fourth radius of curvature, different from the first, second, and third radii of curvature, and a fifth curved edge 512, having a fifth radius of curvature, different from the first, second, third, and fourth radii of curvature. In an exemplary embodiment, first linear edge 502 has a length of about 11.55 mm, first curved edge 504 has a radius of curvature of about 6.56 mm, second curved edge 506 has a radius of curvature of about 5.08 mm, third curved edge 508 has a radius of curvature of about 30 mm, fourth curved edge 510 has a radius of curvature of about 9.09 mm, and fifth curved edge 512 has a radius of curvature of about 2.50 mm.

Figure 33:
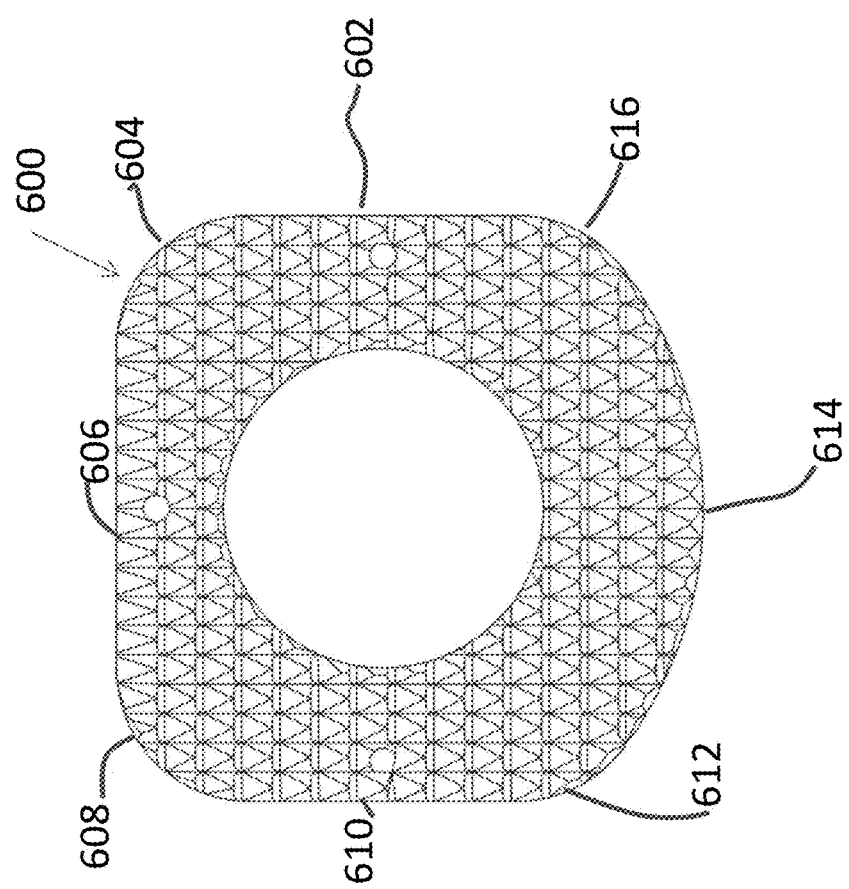
FIG. 33 is a top plan view of the wedge osteotomy implant of FIG. 32, with the bottom plan view being identical.
Figure 36:
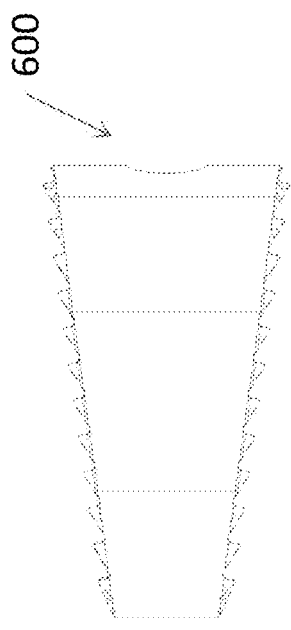
FIG. 36 is a right side elevational view of the wedge osteotomy implant of FIG. 32.
Figure 37:
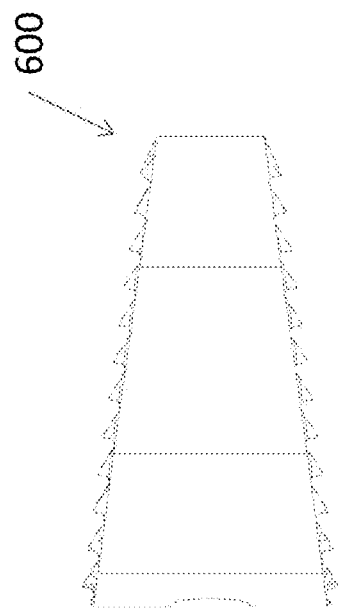
FIG. 37 is a left side elevational view of the wedge osteotomy implant of FIG. 32.
Figure 38:
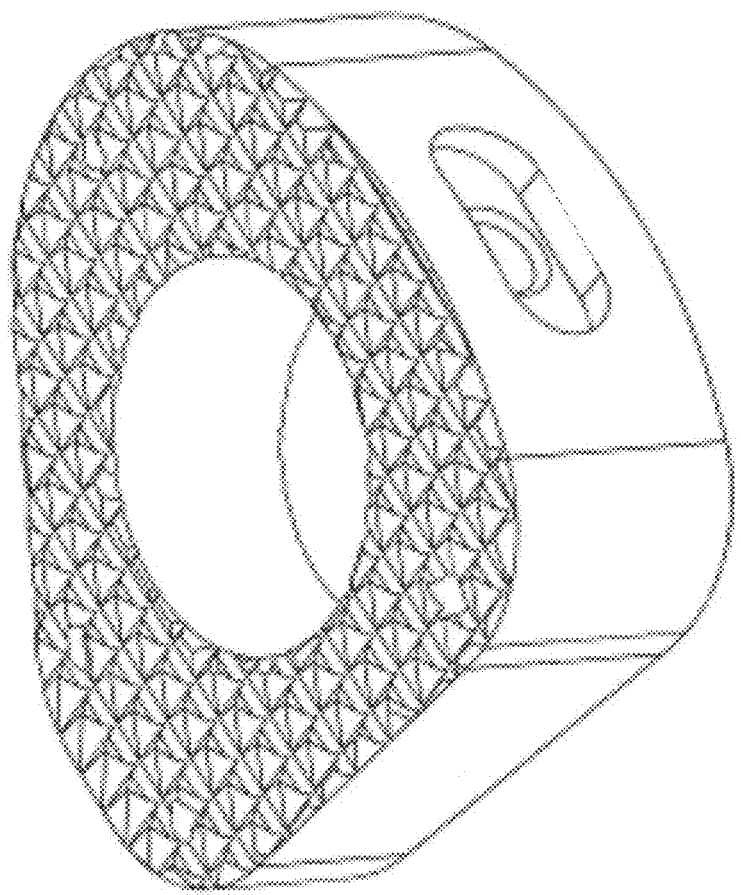
FIG. 38 is a perspective view of a seventh exemplary embodiment of an osteotomy wedge implant according to the present invention.
Figure 42:
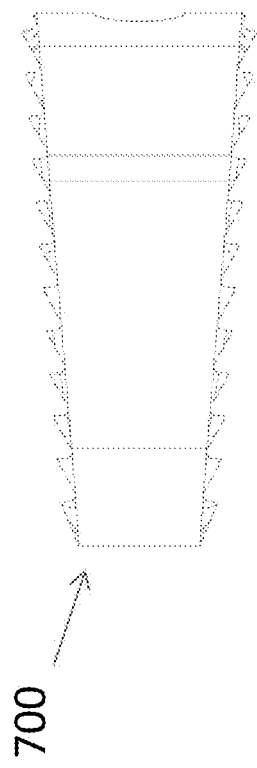
FIG. 42 is a right side elevational view of the wedge osteotomy implant of FIG. 38.
Figure 43:
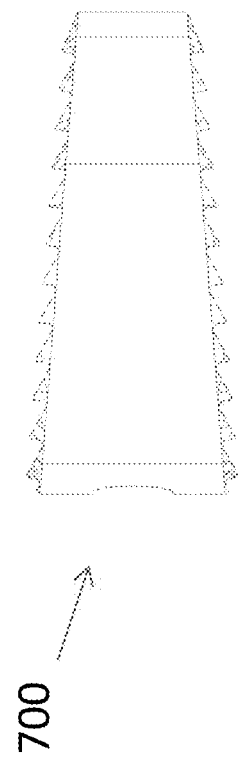
FIG. 43 is a left side elevational view of the wedge osteotomy implant of FIG. 38.

Referring now to FIGS. 32-37, an exemplary embodiment of a wedge 600 is shown. Referring specifically to FIG. 33, wedge 600 has a first linear edge 602, a first curved edge 604 having a first radius of curvature, a second linear edge 606, a second curved edge 608 having the first radius of curvature, a third linear edge 610, the same length as first linear edge 602, a third curved edge 612 having the first radius of curvature, a fourth curved edge 614 having a second radius of curvature, and a fifth curved edge 616 having the first radius of curvature. In an exemplary embodiment, first linear edge 602 and third linear edge 610 each has a length of about 6.89 mm, each of first curved edge 604, second curved edge 608, third curved edge 612, and fifth curved edge 616 has a radius of curvature of about 5 mm, second linear edge 606 has a length of about 8 mm, and fourth curved edge 614 has a radius of curvature of about 15 mm. Additionally, first curved edge 604 and second curved edge 608 each trace arcs of 90 degrees, such that first linear edge 602 and third linear edge 610 are parallel to each other and second linear edge 606 is orthogonal to each of first and third linear edges 602, 610.

Referring now to FIGS. 38-43, an exemplary embodiment of a wedge 700 is shown. Referring specifically to FIG. 39, wedge 700 has a first linear edge 702, a first curved edge 704 having a first radius of curvature, a second linear edge 706, a second curved edge 708 having the first radius of curvature, a third linear edge 710, a third curved edge 712 having a second radius of curvature, a fourth curved edge 714 having the first radius of curvature, a fifth curved edge 716 having a third radius of curvature, and a sixth curved edge 718 having a fourth radius of curvature. In an exemplary embodiment, first linear edge has a length of about 6.82 mm, first, second, and fourth curved edges each has a radius of curvature of about 4 mm, second linear edge has a length of about 1.03 mm, third linear edge 710 has a length of about 8.67 mm, third curved edge has a radius of curvature of about 5 mm, fifth curved edge 716 has a radius of curvature of about 15 mm, and sixth curved edge 718 has a radius of curvature of about 6.63 mm.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. An osteotomy implant system comprising:
a wedge shaped core having a central plane extending therethrough;
a first bone engaging surface extending at an acute angle relative to the central plane on a first side of the core; and
a second bone engaging surface disposed on an opposing side of the central plane from the first bone engaging surface on a second side of the core, the second bone engaging surface extending at the acute angle relative to the central plane,
wherein the first and second bone engaging surfaces comprise an osteoconductive structure, and
wherein the first surface has a perimeter having a plurality of linear edges and wherein the perimeter is shaped such that the core is asymmetrical relative to all axes bisecting and extending perpendicular to each of the plurality of linear edges.

2. The osteotomy implant system according to claim 1, wherein the osteoconductive structure is undetectable by imaging.

3. The osteotomy implant system according to claim 1, further comprising a fixation plate having a first opening and a second opening space from the first opening farther than a distance between the first generally planar bone engaging surface and a second generally planar bone engaging surface.

4. The osteotomy implant system according to claim 3, wherein the core comprises a peripheral portion having a threaded aperture formed therein.

5. The osteotomy implant system according to claim 4, wherein the fixation plate further has a third opening located between the first opening and the second opening such that, when the fixation plate is secured over the core, the third opening is aligned with the threaded aperture.

6. The osteotomy implant system according to claim 1, wherein the at least one of the surfaces has an osteoconductive structure with a thickness of less than 800 microns.

7. The osteotomy implant system according to claim 6, wherein the thickness is between 5 nanometers and 800 microns.

8. The osteotomy implant system according to claim 1, wherein the first generally planar bone engaging surface and the second generally planar bone engaging surface are transparent to imaging.

9. The osteotomy implant system according to claim 1, wherein the first generally planar bone engaging surface and the second generally planar bone engaging surface are visible to imaging.

10. The osteotomy implant system according to claim 1, wherein the osteoconductive structure comprises a titanium plasma spray.

11. The osteotomy implant system according to claim 1, wherein the core is sized and shaped such that at least 50% of the perimeter of the core is contained within an osteotomy site.

12. An osteotomy implant system comprising:
a wedge shaped core;
a first bone engaging surface disposed on a first side of the core; and
a second bone engaging surface disposed on a second side of the core,
wherein the first and second bone engaging surfaces comprise an osteoconductive structure, and
wherein the first surface has a perimeter having a first linear edge, a first curved edge directly attached to the first linear edge and having a first radius of curvature, a second linear edge directly attached to the first curved edge, a second curved edge directly attached to the second linear edge, a third linear edge directly attached to the second curved edge, a third curved edge directly attached to the third linear edge and having a second radius of curvature, a fourth curved edge directly attached to the third curved edge, a fifth curved edge directly attached to the fourth curved edge and having a third radius of curvature, and a sixth curved edge directly attached to the fifth curved edge and having a fourth radius of curvature, wherein each of the first, second, third, and fourth radii of curvature are all different from the others of the first, second, third, and fourth remaining radii of curvature, and
wherein the perimeter is shaped such that the core is asymmetrical relative to all axes bisecting and extending perpendicular to each of the plurality of linear edges.

* * * * *